(12) United States Patent
Ahmed

(10) Patent No.: US 9,005,125 B1
(45) Date of Patent: Apr. 14, 2015

(54) TONOMETER

(76) Inventor: A. Mateen Ahmed, Rancho Cucamonga, CA (US)

( * ) Notice: Subject to any disclaimer, the term of this patent is extended or adjusted under 35 U.S.C. 154(b) by 0 days.

(21) Appl. No.: 13/017,712

(22) Filed: Jan. 31, 2011

Related U.S. Application Data

(60) Provisional application No. 61/301,541, filed on Feb. 4, 2010.

(51) Int. Cl.
*A61B 3/16* (2006.01)

(52) U.S. Cl.
CPC .................................... *A61B 3/16* (2013.01)

(58) Field of Classification Search
CPC ........................................................ A61B 3/16
USPC .......................... 600/398, 399, 405; 351/205
See application file for complete search history.

(56) References Cited

U.S. PATENT DOCUMENTS

| | | | | |
|---|---|---|---|---|
| 4,621,644 A * | 11/1986 | Eilers | | 600/405 |
| 4,622,459 A * | 11/1986 | Bouge et al. | | 250/214 A |
| 4,628,938 A * | 12/1986 | Lee | | 600/405 |
| 4,680,755 A * | 7/1987 | Reames | | 370/451 |
| 4,729,378 A * | 3/1988 | Trittenbass | | 600/398 |
| 4,747,296 A * | 5/1988 | Feldon et al. | | 73/1.62 |
| 4,817,620 A * | 4/1989 | Katsuragi et al. | | 600/401 |
| 4,922,913 A * | 5/1990 | Waters et al. | | 600/398 |
| 4,944,303 A * | 7/1990 | Katsuragi | | 600/401 |
| 5,109,852 A * | 5/1992 | Kaye et al. | | 600/398 |
| 5,148,807 A * | 9/1992 | Hsu | | 600/402 |
| 5,165,408 A * | 11/1992 | Tomoda | | 600/401 |
| 5,165,409 A * | 11/1992 | Coan | | 600/405 |
| 5,197,473 A * | 3/1993 | Fedorov et al. | | 600/398 |
| 5,203,331 A * | 4/1993 | Draeger | | 600/405 |
| 5,638,149 A * | 6/1997 | Machemer et al. | | 351/200 |
| 5,779,633 A * | 7/1998 | Luce | | 600/398 |
| 5,830,139 A * | 11/1998 | Abreu | | 600/405 |
| 5,836,873 A * | 11/1998 | Fresco | | 600/398 |
| 5,865,742 A * | 2/1999 | Massie | | 600/405 |
| 5,889,576 A * | 3/1999 | Fujieda | | 351/208 |
| 5,989,195 A * | 11/1999 | Iijima et al. | | 600/561 |
| 6,042,544 A * | 3/2000 | Miwa et al. | | 600/399 |
| 6,053,876 A * | 4/2000 | Fisher | | 600/562 |
| 6,083,160 A * | 7/2000 | Lipman | | 600/398 |
| 6,113,542 A * | 9/2000 | Hyman et al. | | 600/398 |
| 6,120,460 A * | 9/2000 | Abreu | | 600/558 |
| 6,159,148 A * | 12/2000 | Luce | | 600/405 |
| 6,190,317 B1 * | 2/2001 | Hayafuji | | 600/405 |
| 6,193,656 B1 * | 2/2001 | Jeffries et al. | | 600/398 |
| 6,234,966 B1 * | 5/2001 | Miwa | | 600/401 |
| 6,251,071 B1 * | 6/2001 | Fresco et al. | | 600/398 |
| 6,287,256 B1 * | 9/2001 | Park et al. | | 600/398 |
| 6,361,495 B1 * | 3/2002 | Grolman | | 600/401 |
| 6,394,968 B1 * | 5/2002 | Wallace | | 600/398 |
| 6,409,344 B1 * | 6/2002 | Hayashi | | 351/208 |

(Continued)

OTHER PUBLICATIONS

Moulding and Casting Supplies, Durometer Definition, 2004.*

*Primary Examiner* — Brian Szmal
(74) *Attorney, Agent, or Firm* — John J. Connors; Connors & Assoc. pc

(57) ABSTRACT

A tonometer includes a pair of arms pivotally connected at proximal ends thereof, one arm having a contact member at a distal end. Mounted to the one arm and in contact with the contact member is a pressure transducer providing an electrical signal corresponding to the pressure applied to the contact member. A control circuit responds to the signal to indicate on a visual display the intraocular pressure.

2 Claims, 3 Drawing Sheets

(56) References Cited

U.S. PATENT DOCUMENTS

| | | | |
|---|---|---|---|
| 6,413,214 B1 * | 7/2002 | Yang | 600/405 |
| 6,419,631 B1 * | 7/2002 | Luce | 600/401 |
| 6,423,001 B1 * | 7/2002 | Abreu | 600/405 |
| 6,440,070 B2 * | 8/2002 | Israel | 600/398 |
| 6,447,449 B1 * | 9/2002 | Fleischman et al. | 600/405 |
| 6,524,243 B1 * | 2/2003 | Fresco | 600/399 |
| 6,537,215 B2 * | 3/2003 | Miwa | 600/405 |
| 6,579,235 B1 * | 6/2003 | Abita et al. | 600/398 |
| 6,923,765 B2 * | 8/2005 | Ahmed | 600/399 |
| 2002/0193675 A1 * | 12/2002 | Rathjen | 600/405 |
| 2003/0117580 A1 * | 6/2003 | Franz et al. | 351/205 |
| 2006/0020194 A1 * | 1/2006 | Ahmed | 600/399 |

* cited by examiner

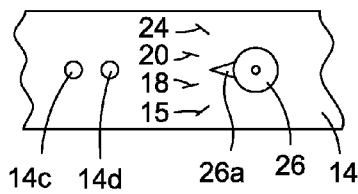
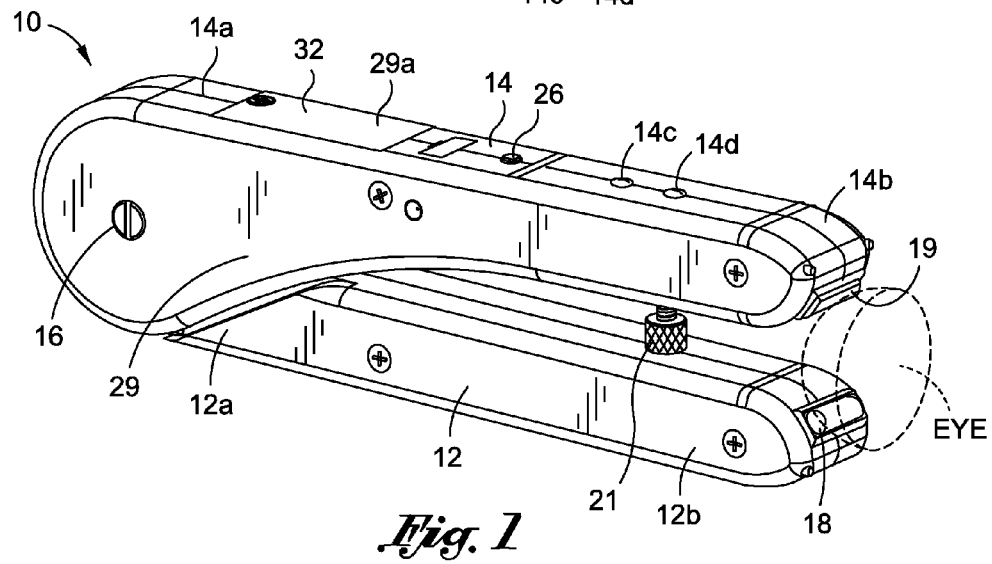
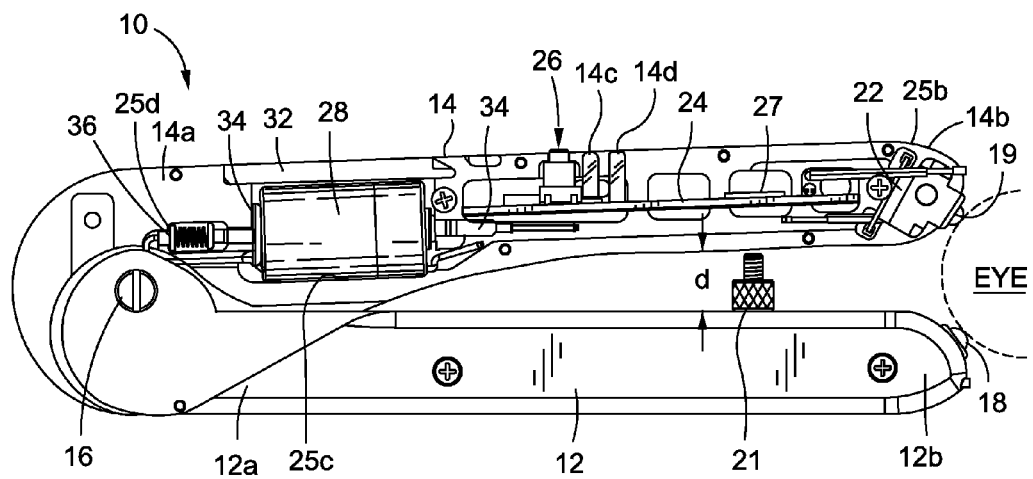

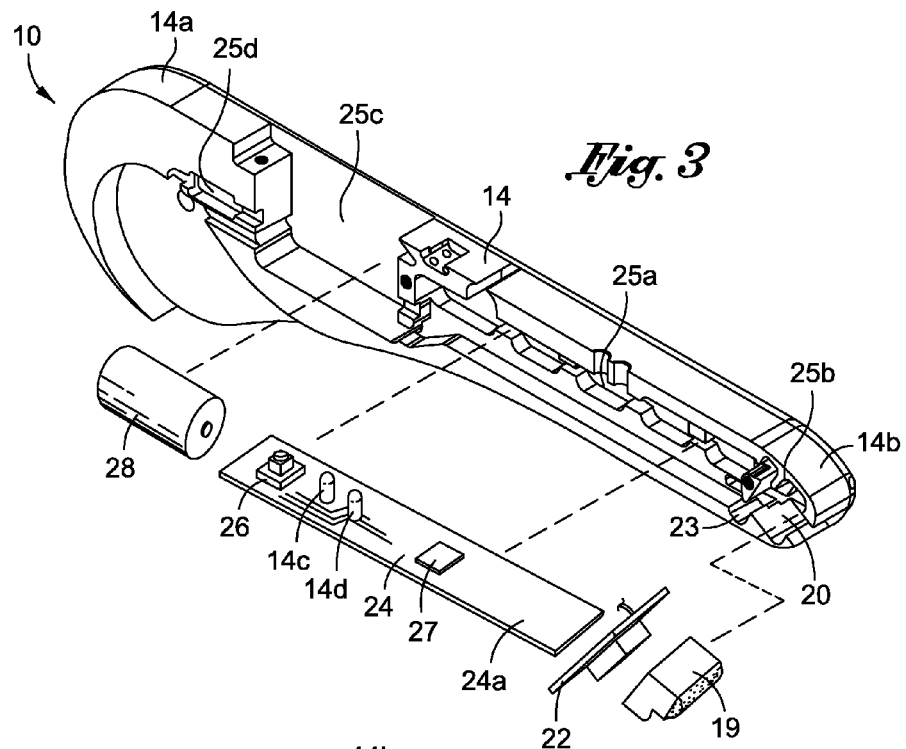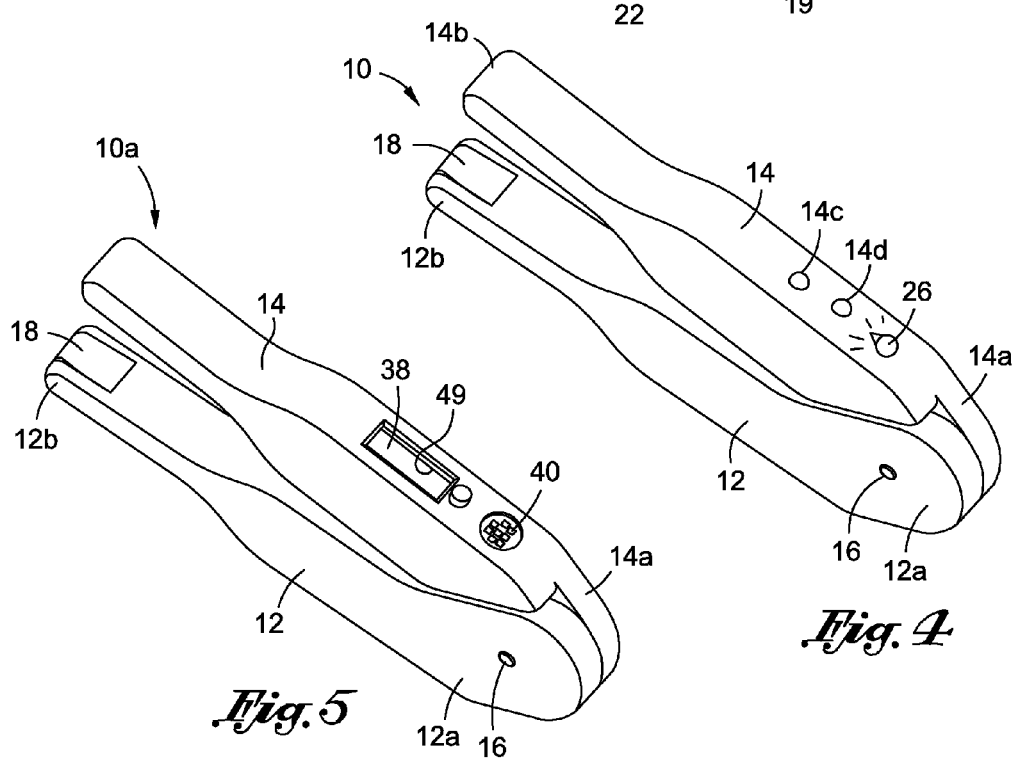

TONOMETER

RELATED APPLICATION AND INCORPORATION BY REFERENCE

This utility application claims the benefit under 35 U.S.C. 119(e) of U.S. Provisional Patent Application No. 61/301,541, entitled "Tonometer," filed Feb. 4, 2010. This related application is incorporated herein by reference and made a part of this application. If any conflict arises between the disclosure of the invention in this utility application and that in the related provisional application, the disclosure in this utility application shall govern. Moreover, any and all U.S. patents, U.S. patent applications, and other documents, hard copy or electronic, cited or referred to in this application are incorporated herein by reference and made a part of this application.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

The words "substantially" and "essentially" have equivalent meanings

BACKGROUND

Tonometers are well-known devices for detecting the intraocular pressure within an eye. There are several types of tonometers available. In general, the commercially available tonometers require that the eyelid be open, and a contact directly or indirectly is made with the open eye. For example, one type of tonometer uses a jet of gas that impinges against the open eye. Another type has a probe that makes physical contact with the open eye. Such conventionally tonometers are expensive, and not particularly accurate. Moreover, their use frequently irritates the patient's eye. Consequently, it would be desirable to provide a tonometer that could detect the intraocular pressure through the closed eyelid of a patient. In U.S. Pat. No. 7,288,067 such a tonometer is disclosed.

SUMMARY

My tonometer disclosed herein is an improvement in the tonometer disclosed in U.S. Pat. No. 7,288,067 and has one or more of the features depicted in the embodiments discussed in the section entitled "DETAILED DESCRIPTION OF SOME ILLUSTRATIVE EMBODIMENTS." The claims that follow define my tonometer, distinguishing it from the prior art; however, without limiting the scope of my tonometer as expressed by these claims, in general terms, some, but not necessarily all, of its features are:

One, my tonometer for measuring the intraocular pressure of an eye includes a pair of arms connected at proximal ends thereof to pivot, and a solid state contact member at a distal end of one of the arms. The arms are manually moveable between an open position where distal ends of the arms are separated to enable the distal ends to be manually positioned against an eye and a measuring position where the arms are manually moved towards each other while in contact with the eye so the distal ends are at a predetermined distance from each other to apply essentially the same external pressure against the eye with each measurement of intraocular pressure. A stop member may be between the arms. The stop member limits the distance the distal ends of the arms may be moved manually towards each other to apply essentially the same external pressure against the eye with each measurement of intraocular pressure.

Two, the solid state pressure transducer provides an electrical signal corresponding to the intraocular pressure of an eye in response to the contact member being pressed against an eye being tested. The eyelid may be closed during testing of the intraocular pressure and the contact member is pressed directly against the eyelid. The contact member may be a resilient pad in physical contact with the pressure transducer, having, for example, a Shore durometer substantially from 5 to 50 units. The pressure transducer may be disposed at or within the distal end of an arm. The transducer provides an electrical signal in proportion to the deflection of the contact member, which deflects in proportion to the magnitude of the intraocular pressure of the eye being measured.

Three, an electronic control circuit may be disposed within an arm. This circuit includes a microprocessor that is programmed to control the operations of the tonometer in response to the electrical signal. My tonometer may include (a) a memory element that stores intraocular pressure measurement data, and (b) a cable attachment port connected to the control circuit that is accessible to a computer cable for downloading intraocular pressure measurement data stored in the memory element. The cable attachment port is electrically connected to the control circuit. An arm may include a battery storage compartment to hold a battery that provides electrical power to the circuit. The microprocessor is electrically connected to the transducer to receive the signal and is programmed to provide on a display an indication of the intraocular pressure as determined by the signal.

Four, my tonometer includes a display responsive to the electrical signal to indicate the intraocular pressure of an eye upon pressing the eye between distal ends of the arms. The display may be a visual display connected to the control circuit that provides a readout corresponding to the electrical signal. For example, the visual display may comprise a first light of one color that indicates when lit that the intraocular pressure is safe and a second light of another color that indicates when lit that the intraocular pressure is unsafe. The visual display, in addition to or alternatively, may provide a numerical or alpha-numerical readout of the intraocular eye pressure.

DESCRIPTION OF THE DRAWING

Some embodiments of my tonometer are discussed in detail in connection with the accompanying drawing, which is for illustrative purposes only. This drawing includes the following figures (Figs.), with like numerals indicating like parts:

FIG. 1 is a perspective view of one embodiment of my tonometer looking at the distal ends of its arms.

FIG. 1A is a fragmentary plan view of one arm of the embodiment shown in FIG. 1.

FIG. 2 is a side view of the embodiment shown in FIG. 1 with a sidewall of an arm removed.

FIG. 3 is an exploded perspective view of one arm of the embodiment shown in FIG. 1.

FIG. 4 is a perspective view of the embodiment of my tonometer shown in FIG. 1 looking at the proximal ends of the arms of my tonometer pivotally connected together and employing a display having lights that are selectively energized to indicate that the intraocular pressure is at a safe level or above a safe level.

FIG. 5 is a perspective view of another embodiment of my tonometer that provides a digital readout of the intraocular pressure.

DETAILED DESCRIPTION OF SOME ILLUSTRATIVE EMBODIMENTS

General

Figure 6:
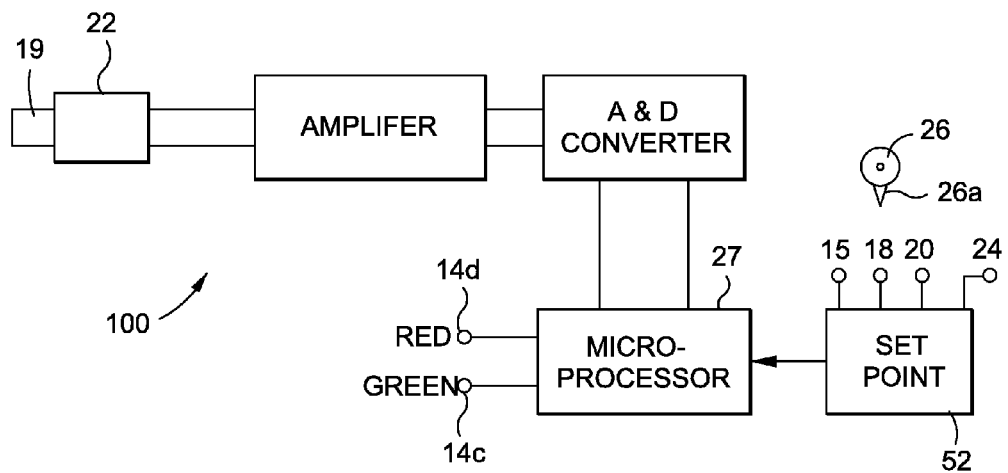
FIG. 6 is a schematic diagram of a control circuit for the embodiment of my tonometer depicted in FIGS. 1 through 4.

Two embodiments of my tonometer are illustrated, one shown in FIGS. 1 through 4 and identified generally by the numeral 10, and another shown in FIG. 5 and identified generally by the numeral 10a. Both embodiments have substantially identical features except for the method of displaying measured intraocular pressure readings. These embodiments, tonometers 10, 10a, each includes a pair of rigid, substantially straight arms 12 and 14 having disconnected, free distal ends 12b and 14b, respectively, and respective proximal ends 12a and 14a pivotally connected by a pinion 16. Both arms 12 and 14 may be molded from a plastic material such as thermoplastics and condensation polymers, for example, polypropylene. The arm 14 has a detachable sidewall 29 (FIG. 1) that covers a plurality of compartments that hold the various electrical components of my tonometers 10, 10a.

The arms 12 and 14 are manually moveable between an open position (not shown) with the distal ends 12b and 14b widely separated and, as shown in FIG. 1, a measuring position (FIG. 1) where the distal ends are close to each other but separated by a fixed, predetermined distance d (FIG. 2). A rigid contact element 18 is at the distal end 12b and a deformable contact member 19 comprising a resilient pressure pad 19 is at the distal end 14b. The resilient pad 19 is a sheet of material that is substantially softer than the eyeball so the pad deflects rather than the eyeball when the pad initially contacts the eye ball. For example, the pad 19 has a Shore durometer substantially from 5 to 50 units. The thickness of the sheet material is substantially from 0.1 to 0.2 inch and it has a substantially planar contact area substantially from 0.4 to 0.6 square inch. As shown in FIGS. 2 and 3, a solid state pressure transducer 22, a substantially planar piezoelectric crystal, is in intimate physical contact with the resilient pressure pad 19, which deforms when pressed firmly against a closed eye lid as depicted in FIG. 1. This combination of a resilient pad 19 and piezoelectric crystal transducer 22a detects the pressure the eye exerts against pressure pad when the arms 12 and 14 are in the measuring position. This pressure transducer 22 is one of the components of control circuits 100 and 200 depicted in FIGS. 6 and 8, respectively, for the two embodiments of my tonometers 10 and 10a.

As shown in FIGS. 1 and 2, a stop member 21 disposed at an intermediate position between the arms 12 and 14 is attached, for example, to the arm 12. This stop member 21 limits the inward movement of the arms 12 and 14 towards each other to separate them by the distance d. The arms 12 and 14 are thus manually moveable between the open position and the measuring position (FIG. 1) where the pads 18 and 19 bear against the opposed lateral sides of an eyelid of a closed eye. While in contact with the eyelid the distal ends 12b and 14b are at the same predetermined distance d from each other for each measurement of intraocular pressure to apply essentially the same external pressure against the eyelid with each such measurement.

All my tonometers 10, 10a have a display indicating the intraocular pressure of an eye upon pressing the eye between the distal ends 12b and 14b of the arms 12 and 14. As illustrated in FIG. 4, the tonometer 10 employs a green light 14c and a red light 14d. As the user applies pressure against the eye by moving together the arms 12 and 14, the green light 14c is illuminated if the intraocular pressure is at a safe level, for example, at an intraocular pressure substantially from 5 millimeter (mm) of mercury (Hg) to 60 mm of Hg. If the intraocular pressure is at an unsafe elevated level, the red light 14d is illuminated.

Figure 7:
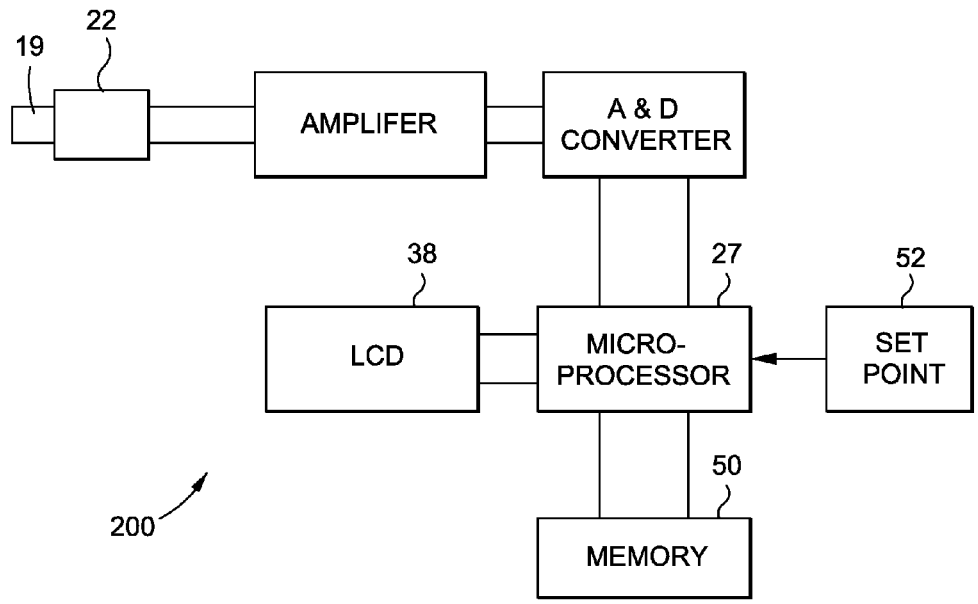
FIG. 7 is a schematic diagram of a control circuit for the embodiment of my tonometer depicted in FIG. 5.

As illustrated in FIGS. 5 and 7, my tonometer 10a has a liquid crystal display 38 in lieu of the green light 14c and red light 14d. The liquid crystal display 38 provides a digital readout, for example, a numerical or alpha-numerical readout of the intraocular eye pressure on the liquid crystal display screen 38. In the tonometer 10, the arm 14 is designed to accommodate the display using the two lights 14c and 14d. In the tonometer 10a, the arm 14 is designed to accommodate the display using the liquid crystal display screen 38. Consequently, the arms 14 have slightly different characteristics and will be discussed separately in the following sections:

Arm 14 for Tonometer 10

As best shown inn FIGS. 2 and 3, the arm 14 in the tonometer 10 has hollow portions functioning as compartments 25a, 25b, 25c, and 25d for the electrical components of the control circuits 100 (FIG. 6) and 200 (FIG. 7). A generally flat, planar circuit board 24 is disposed lengthwise in the central compartment 25a. The pressure transducer 22, a microprocessor 27, the lights 14c and 14d, a reset dial 26, a set point circuit 52, and the pressure transducer 22 are mounted to the circuit board 24. The central compartment 25a is shaped to accommodate the size and shapes of the different components on the circuit board 24. The circuit board 24, with the components thereon, is inserted into this compartment 25a after removal of a detachable sidewall 29 (FIG. 1) of the arm 14. The pressure transducer 22 is adjacent to a distal end 24a of the circuit board 24. Opposed edges of the pressure transducer 22 are received in internal slots in the compartment 25b, positioning the substantially flat or planar face of the transducer next to and abutting the substantially flat or planar underside of the pressure pad 19. Thus, the abutting surfaces of the pressure transducer 22 and the pressure pad 19 make intimate physical contact to insure that the pressure detected by deflection of the pad is transmitted to the transducer, which then generates an electrical signal proportional to the detected pressure. The lights 14c and 14d and reset dial 26 partially protrude through openings in a topside 29a of the arm 14.

The set point circuit 52 is designed to provide an adjustable set point for actuation of the lights 14c and 14d. The reset dial 26 enables the set point to be manually selected for individual patients, for example, by an eye doctor. For example, as illustrated in FIG. 1A, there are four settings indicated by the numerals 15, 18, 20, 24 that correspond to intraocular pressures. The reset dial 26 is shown with its pointer 26a at the numeral 18 indicating that the set point is 18 psi. Thus, if the intraocular pressure exceeds 18 psi, the red light 10d is illuminated. Manually turning the reset dial 26 so that its pointer 26a points to another setting, for example, the numeral 24, resets the set point so that, if the intraocular pressure exceeds 18 psi, the red light 10d is illuminated.

A battery 28 fits inside the compartment 25c and provides power to the circuits 100 and 200, as the case may be. A detachable battery compartment door 32 covers the battery compartment 25c and allows the users to replace battery 28. A metallic connector 34 seated in the compartment 25c connects the terminals of the battery 28 to the control circuits, providing electrical energy to the electrical components mounted to the circuit board 24. A spring 36 is disposed within the compartment 25*d* exerts a force on the metallic connector 34 to insure good electrical contact between the battery terminals and the metallic connector 34.

Arm 14 for Tonometer 10*a*

As best shown inn FIGS. 5 and 7, the arm 14 in the tonometer 10*a* has a window 49 holding a liquid crystal display, a memory 50, an electronic set point control circuit 52*a*, and computer attachment port 40. The computer attachment port 40 is connected to the circuit board 24 and enables, for example, a computer cable (not shown) to be connected to the computer attachment port 40 to upload intraocular eye pressure measurement data stored in a memory element 50 into the eye doctor's data storage system (not shown). Also the attachment port 40 enables communication between the doctor's computer (not shown) and the tonometer 10*a* so that the doctor may electronically adjust the set point control circuit 52*a*. For example, set point commands or data to or from the doctor's computer for storage in a memory device may be sent over the internet computer network or via Blue Tooth or Zig-bee within a few hundred feet of a transmitter. Although a computer cable may be used for communication between the tonometer 10*a* and the doctor's computer, a wireless connection may also be used.

SCOPE OF THE INVENTION

The above presents a description of the best mode I contemplate of carrying out my tonometer, and of the manner and process of making and using it, in such full, clear, concise, and exact terms as to enable any person skilled in the art to which it pertains to make and use my tonometer. My tonometer is, however, susceptible to modifications and alternate constructions from the illustrative embodiments discussed above which are fully equivalent. Consequently, it is not my intention to limit my tonometer to the particular embodiments disclosed. On the contrary, my intention is to cover all modifications and alternate constructions coming within the spirit and scope of my tonometer as generally expressed by the following claims, which particularly point out and distinctly claim the subject matter of my invention:

The invention claimed is:

1. A tonometer for measuring the intraocular pressure of an eye with the eyelid closed, said tonometer including
    a pair of arms, said arms pivotally connected at proximal ends thereof, and each arm having a distal end,
    said arms being manually moveable between an open position where the distal ends are separated to enable said distal ends to be manually positioned against the closed eyelid and a measuring position where the arms are manually moved towards each other while in contact with the closed eyelid so the distal ends are at a predetermined distance from each other to apply the same external pressure against the eye with each measurement of intraocular pressure,
    a resilient pad attached to a distal end of one arm, said pad positioned to make physical contact with a closed eyelid of the eye being tested and be deformed when the arms are moved to the measuring position,
    a solid state pressure transducer disposed within the one arm, said transducer being a piezoelectric crystal in intimate physical contact with the resilient pad,
    said transducer configured to provide an electrical signal in proportion to the deflection of the pad that corresponds to the intraocular pressure of the eye being tested in response to the resilient pad being pressed against the closed eyelid of said eye being tested, and
    a control circuit including a micro-processor, said transducer and a display to indicate the intraocular pressure of the eye.

2. The tonometer of claim 1 where resilient pad is a sheet of material that is softer than an eyeball of the eye being tested so the pad deflects rather than the eyeball during measurement.

* * * * *